United States Patent [19]

Stavrianpoulos

[11] Patent Number: 4,767,609

[45] Date of Patent: Aug. 30, 1988

[54] THERAPEUTIC AND DIAGNOSTIC PROCESSES USING ISOTOPE TRANSFER TO CHELATOR-TARGET RECOGNITION MOLECULE CONJUGATE

[75] Inventor: Jannis G. Stavrianpoulos, New York, N.Y.

[73] Assignee: Enzo Biochem, Inc., New York, N.Y.

[21] Appl. No.: 6,818

[22] Filed: Jan. 23, 1987

Related U.S. Application Data

[62] Division of Ser. No. 575,397, Jan. 30, 1984.

[51] Int. Cl.$^4$ ...................... A61K 43/00; A61K 49/00
[52] U.S. Cl. .......................................... 424/1.1; 424/9; 424/85; 424/88; 424/89; 424/92; 530/350; 530/402; 530/403; 530/405; 530/406; 536/1.1; 536/26; 536/27; 536/28; 422/61
[58] Field of Search .................... 424/1.1, 9, 85, 88, 424/89, 92; 530/350, 402, 403, 405, 406; 536/1.1, 26–28; 422/61

[56] References Cited

U.S. PATENT DOCUMENTS

| | | | |
|---|---|---|---|
| 3,936,440 | 2/1976 | Nath | 536/25 |
| 4,043,998 | 8/1977 | Meares et al. | 260/501.1 |
| 4,057,615 | 11/1977 | Bardy et al. | 424/1.1 |
| 4,272,503 | 6/1981 | Camin et al. | 424/1.1 |
| 4,305,922 | 12/1981 | Rhodes | 424/1.1 |
| 4,645,660 | 2/1987 | Takahashi et al. | 424/9 |

OTHER PUBLICATIONS

Meares et al., *Proc. Nat. Acad. Sci. U.S.A.*, 69, 3718–3722 (1972).
DeRiemer et al., *J. Med. Chem.*, 22, 1019–1023 (1979).

*Primary Examiner*—Christine M. Nucker
*Attorney, Agent, or Firm*—Charles J. Herron

[57] ABSTRACT

A method of forming a therapeutic or diagnostic agent labeled with a radioactive metal ion, which comprises: contacting an unlabeled therapeutic or diagnostic agent, consisting of a substantially non-metal chelating portion and a chelating portion capable of chelating with the radioactive metal ion, with an ion transfer material having the radioactive metal ion bound thereto and having a binding affinity for the radioactive metal less than the binding affinity of the chelating portion for the radioactive metal ion, wherein prior to contacting the chelating portion is unchelated or is chelated with a second metal having a binding affinity with the chelating portion less than the binding affinity of the radioactive metal ion, whereby a radiolabeled therapeutic or diagnostic agent is formed by the contacting, and separating the radiolabeled therapeutic or diagnostic agent from the ion transfer material, is disclosed along with various components and kits useful in practicing this method and several variations thereof.

27 Claims, No Drawings

THERAPEUTIC AND DIAGNOSTIC PROCESSES USING ISOTOPE TRANSFER TO CHELATOR-TARGET RECOGNITION MOLECULE CONJUGATE

This is a division of application Ser. No. 575,397, filed Jan. 30, 1984.

BACKGROUND OF THE INVENTION

1. Field of the Invention

The present invention relates to methods of radioactively labeling diagnostic and therapeutic agents and is particularly related to systems in which a metal ion is bound to the labeled molecule through a chelating group.

2. Description of the Prior Art

The use of radioactively labeled diagnostic and therapeutic agents has become routine practice in clinical and analytical laboratories throughout the world. Such radioactively labeled compounds are used both in vitro (for example, in radioimmunoassay systems) and in vivo (for example, both in diagnostic imaging techniques and in radiation therapy techniques).

Initially, the number of radioisotopes that could be firmly attached to the typical organic molecules used as diagnostic and therapeutic agents was limited. The difficulty in forming stable carbon-metal bonds prevented the early utilization of many radioactive metals and typically limited radioisotopes used to label organic molecules to isotopes of phosphorus, carbon, hydrogen, and iodine.

Recently, a new approach has enabled the labeling of such agents with metal ions. In this approach, a chelating moiety is covalently attached to the molecule of interest, and a radioactive ion is then chelated by the sequestering groups of the chelator. The chelating moieties which have generally been used for this purpose in the prior art have been analogues or derivatives of ethylenediaminetetraacetic acid (EDTA), although many variations have also occurred. For example, in 1968, W. F. Benisek and F. M. Richards suggested the covalent bonding of chelating groups based on methylpicotinimidate to the amino function of a protein molecule in order to facilitate crystallographic investigation of protein structure by binding a metal to the chelating site on the protein [J. Biol. Chem., 243 4267–4271 (1968)]. Likewise, in U.S. Pat. No. 4,043,998, the compound 1-(p-benzenediazonium)ethylenediaminetetraacetic acid, said to be a powerful chelating agent which can be bonded strongly to proteins through its diazonium group, was disclosed. In Science, 209, 295–297 (1980), B. A. Khaw et al. disclosed the use of a bifunctional chelating agent, diethylenetriaminepentaacetic acid (DTPA) to label an antibody with a radioactive isotope and the subsequent use of that labeled antibody to image experimental myocardial infarctions in dogs. The metal binding efficiencies of the resulting compounds were low, however, since attachment occurred through one of the carboxylate groups which would normally have participated in binding to the metal ion. Similarly, D. A. Scheinberg and O A. Gansow taught in Science, 215 1511–1513 (1982), the use of DTPA and EDTA analogs covalently bonded to antibodies to image mouse erythroid tumors.

Unfortunately, the radioactively labeled materials previously available suffered from several disadvantages. This was particularly true for imaging agents and other molecules labeled with an isotope of high specific activity. The short half-lives of the radioactive isotopes used and the radiation-induced degradation of the labeled molecules greatly reduced the shelf-lives of these materials and, when imaging agents are involved, greatly increased the amount of background radiation present. Furthermore, health hazards to the technicians handling these materials and hazards associated with disposing of the associated waste generated at various steps of synthesizing labeled compounds made the handling of radioactively labeled compounds difficult.

Typically, as disclosed by Scheinberg and Strand in the article cited above, a bifunctional chelate was coupled to a target molecule, after which any metal ions present were removed by dialysis, typically against a solution containing low molecular weight chelating molecules such as EDTA. The chelate-conjugated molecules were then labeled with a radioactive metal solution, after which free metal was removed, for example, by ion-exchange chromatrography. The resulting labeled product was then stored and later used in the diagnostic or therapeutic process. Using such procedures, considerable handling of the radioactive material and generation of radioactive waste occurred, a disadvantage not overcome by any teachings of the prior art.

SUMMARY OF THE INVENTION

The present invention provides a universal method which can be used to radioactively label any diagnostic or therapeutic agent having a ligand portion thereof which is capable of binding with a radioactive metal ion. The labeling occurs immediately prior to the utilization of the agent and produces little or no radioactive waste.

The invention provides a method of radioactively labeling a diagnostic or therapeutic molecule with a radioactive metal ion, which comprises:

(A) contacting
  (1) an unlabeled therapeutic or diagnostic agent comprising
    (a) a substantially non-metal chelating portion attached to
    (b) a chelating portion capable of substantially chelating with said radioactive metal ion, with
  (2) an ion transfer material having said radioactive metal ion bound thereto and having a binding affinity of said chelating portion for said radioactive metal ion,
  wherein prior to said contacting said chelating portion is unchelated or is chelated with a second metal ion having a binding affinity with said chelating portion less than the binding affinity of said radioactive metal ion, whereby a radiolabeled therapeutic or diagnostic agent is produced by said contacting; and (B) separating said radiolabeled therapeutic or diagnostic agent from said ion transfer material.

Additionally, the labeling method described above can be used as the first step of a diagnostic or therapeutic process, after which the normal steps of the process are carried out in their usual fashion. Typical of such processes are radioimmunoassay and in vivo diagnostic and therapeutic techniques.

The invention provides, in addition to the aforementioned process, various elements and components to be used therein in the form of kits comprising these components and other components used in the various processes.

In essence, the invention is based on the discovery that, if conditions are properly selected, hazards involving radioactive waste and radioactive products can be ameliorated by utilizing an ion transfer process as the last step prior to the ultimate use of a therapeutic or diagnostic molecule having a radiolabel. Thus, the necessity of handling radioactive material during the preparation of a diagnostic or therapeutic molecule is avoided and no waste radioactivity is generated in the clinical or analytical laboratory environment. Uses for the process, system, and components of the present invention are unlimited and include all of the uses to which prior art techniques involving radiolabeled diagnostic and therapeutic molecules have been put as well as other uses disclosed herein.

DESCRIPTION OF THE PREFERRED EMBODIMENTS

The terms "therapeutic or diagnostic agent" as used in the specification and claims of this application includes any substance or substances either alone or in mixtures which, when labeled with a radioactive metal ion, can be used in the treatment of a disorder of an animal or human body, in an in vivo diagnostic technique involving a human or animal body, or in an in vitro diagnostic technique for any analyte whose detection is desired. Typical of therapeutic agents are radioactive drugs containing beta-emitting radionuclides which are used for therapeutic purposes. These agents localize in pathological tissue and destroy it by ionizing radiation. In vivo diagnostic agents typically incorporate a gamma-emitting nuclide which, because of the physical or metabolic properties of the molecularly recognizable portion of the agent, localizes in a specific organ after administration. Diagnostic images reflecting organ structure and/or function can then be obtained by means of detection devices that detect the distribution of ionizing radiation emitted by the nuclide. In vitro diagnostic agents are exemplified by radioimmunoassay agents which are in wide-spread clinical use. These agents are employed in the measurement of minute quantities of various biological substances, such as hormones.

Diagnostic and therapeutic agents of the invention have two functionally different portions of the molecule or molecular conjugate (although these may be at least in part the same structural portions in some molecules). These portions are (a) a substantailly non-metal chelating portion attached to (b) a chelating portion capable of chelating with the radioactive metal ion being used. By "substantially non-metal chelating portion" is meant to include not only molecular portions which carry no metal-chelating groups, but also molecular portions which may carry certain groups capable of metal chelation but which do so with substantially less affinity than portion (b), the "helating portion."

Particularly preferred among the "substantially non-metal chelating portions" (a) are those which are molecularly recognizable portions. The phrase "molecularly recognizable portion" denotes any molecular portion of the total molecule which is capable of being recognized by a complementary system or molecule in the system in which the agent is being used. Molecular recognition, as will be understood by those skilled in the art, includes the non-covalent binding in three dimensions between complementary portions of two molecules. A molecularly recognizable portion on an agent may be of low molecular weight (about less than MW 2,000) or of high molecular weight. For example, it dan be a polynucleotide sequence, such as RNA or DNA, to be recognized by its complementary sequence; an antigen portion (e.g., a drug, a pesticide, a metabolite, a physiologically occurring compound), to be recognized by its corresponding monoclonal or polyclonal antibody; an antibody portion, to be recognized by its corresponding antigen; a lectin portion, to be recognized by its sugar; a sugar portion, to be recognized by its lectin; a hormone portion, to be recognized by its receptor; a receptor portion, to be recognized by its hormone; an inhibitor portion, to be recognized by its enzyme; an enzyme portion, to be recognized by its inhibitor; a cofactor portion, to be recognized by a cofactor enzyme binding site; a cofactor enzyme binding site portion, to be recognized by its cofactor; a binding ligand, to be recognized by its substrate and vice versa (e.g., biotin-avidin); or any permutation or combination thereof. Among the most common molecularly recognizable portions are the three-dimensional protein arrangements in antigens and antibodies of various sorts, the cell wall structures present in various cells, and the nucleic acid sequences present in the DNA and RNA of organisms. It is preferred in many circumstances that the molecularly recognizable portion be either a natural constituent of a biological system or recognizable by a natural constituent of a biological system. Thus, in a competitive radioimmunoassay using a solid phase antibody which binds to a natural constituent present in the serum of a human or animal, the molecularly recognizable portion preferably would have the same structural features present in the natural component with which it was in competition for binding with the antibody. In a therapeutic agent designed to concentrate radioactivity in a specific tissue, the molecularly recognizable portion would be recognizable by a natural component of that tissue. However, it is the function of being molecularly recognizable that is important rather than the actual structure. For example, the molecularly recognizable portion could be an analog or an artifical component which binds more tightly than any natural component of a biological system and therefore is more selective for a particular tissue or other component of a biological system. Additionally, both the molecularly recognizable portion and the component which recognizes this portion may be entirely artificial, particularly in an in vitro diagnostic assay. As used in this application, the phrase "complementary substance" refers to the component which recognizes the molecularly recognizable portion of the agent, whether the complementary substance is of artificial or biological origin.

Furthermore, the molecularly recognizable portion need be only a small part of the therapeutic or diagnostic agent and further need not correspond to an entire molecule present in any system. For example, when the molecularly recognizable portion is proteinaceous, it may be a relatively short sequence of amino acids found within a much larger sequence of amino acids as would be typical for a hapten or binding site which formed part of a large protein.

The second essential portion of the agent is the "chelating portion." Chelates are coordination complexes that are formed between a metal ion and a ligand that contains at least two electron-donating groups arranged so that a ring structure is formed upon coordination. Especially stable are chelates containing 5- or 6-membered rings. Typical functional groups involved in chelation include acidic or anionic groups derived from carboxylic acids, oximes, hydroxyl compounds, phenols, sulfonic acids, and mercaptans. Uncharged functional groups capable o being involved in chelation include amines (primary, secondary and tertiary), carbonyl groups, thiocarbonyl groups, nitroso groups, and cyclic amines, such as those typically present in heterocyclic compounds. A ligand involved in complexation can be either charged or uncharged.

The chelating portion of the agent typically will be formed by reacting a derivative of a known chelating agent with a molecule having a portion that forms the substantially non-metal chelating portion of the final therapeutic or diagnostic agent. Preferred are chelating portions which comprise a diamine wherein the two amine groups are substituted with two acetic acid moieties, with the two amino groups and/or the four acetic acid groups being capable of donating an electron pair to the same metal ion. Typically, the amino groups will be covalently attached to adjacent carbon atoms. Preferred are derivatives of ethylenediaminetetraacetic acid and other chelating groups having a binding constant for any radioactive metal ion at least as great as that of EDTA for the same metal ion. The ethylenediaminetetraacetic acid derivative 1,2-diaminocyclohexaneacetic acid and its derivatives and analogs are especially preferred. By derivatives and analogs is meant compounds having the basic skeletal structure and functional groups of these compounds but having additional functional groups which do not prevent the resulting compounds from functioning as chelating groups. Typical chelating molecules which can be modified to form the chelating portion of the agent are DCTA, EDTA, tartaric acid, alpha-benzoin oxime, 1,10-phenanthroline, and similar well known compounds.

The substantially non-metal chelating portion of the molecule may be derived from any molecule of small or high molecular weight, any molecular complex, or any biological system (e.g., a virus, a cell or a group of cells). Among the common molecules which may be used as sources are amino acids, saccharides, nucleotides, proteins, polysaccharides, lipopolysaccharides, protein complexes, single- or double-stranded nucleic acids or segments thereof, whole viruses or viral compounds such as cores or capsids, bacteria, tissue cells, and the like. Among the most common proteins are the structural proteins, enzymes, immunoglobulins, and fragments thereof. Among the most common nucleic acids are DNA and RNA of various types, such as tRNA, mRNA, rRNA, and the like. Bacteria, either whole or fragments thereof, such as cell walls or other recognizable portions, include both gram positive and gram negative bacteria. Fungi, algae, viruses and other microorganisms (and fragments thereof) are also included as well as animal (e.g., mammalian) cells including red blood cells.

Because the principal aspect of the present invention contemplates labeling a preformed therapeutic or diagnostic molecule consisting of a non-chelating portion and a chelating portion, the general techniques of producing such molecules are not considered part of the present invention, although certain types of chelating groups and methods of attaching them to the non-chelating portion of agents are discussed in later sections for purposes of illustration.

As discussed in the section of this application entitled prior art, many therapeutic and diagnostic agents having chelating portions and non-chelating portions are already known. For example, Hnatowich et al., Science, 220, 613–615 (1983), which is herein incorporated by reference, disclose a method of covalently coupling the chelator diethylenetriaminepentacetic acid (DPTA) to proteins, such as immunolobulins. Generally, a dianhydride of DTPA is reacted with a molecularly recognizable protein under straightforward conditions. This method may be used to attach a ligand to any molecule having an amino or hydroxyl group or a similar nucleophilic group. Since many molecules already contain one of these groups (and the remainder can generally be easily modified so that they do), this provides a general method of attaching a chelating group to any molecule of interest. Many similar methods, such as those disclosed in the references cited in the section of this application entitled "Description of the Prior Art," all of which are herein incorporated by reference, disclose further ligands and methods of modifying other molecules with them.

In addition to those agents previously known to the prior art, many other diagnostic and therapeutic agents having a moleculary recognizable portion and a chelating portion can be synthesized by standard techniques of organic chemistry. For example, although the prior art has dealt with the attachment of chelating groups to proteins, it is also possible to attach chelating groups to non-proteinaceous molecules of interest, such as lipids, hormones, and sugars. Although chelating groups have not previously been attached to such molecules, many derivatives of these various classes of biological compounds are known which have covalent bonds formed through a carbon, oxygen, nitrogen or sulfur atom to an organic radical not normally part of the compound. Minor variations of the techniques used to snythesize these known compounds can be used to attach chelating groups to the recognizable molecules.

Likewise, chelating molecules can be modified by standard chemical techniques to provide a functional group through which attachment to the recognizable molecule can take place. Several procedures are disclosed for the chelating groups that have been previously modified for attaching to proteins, as has been previously discussed. Furthermore, since many chelating molecules contain at least one radical derived from acetic acid, these molecules can easily be modified using standard techniques to create a functional group on the alpha carbon through which attachment can take place to recognizable molecule. The properly functionalized recognizable molecules and chelating groups can easily be attached one to the other by standard reactions of organic chemistry although, naturally, all the resulting compounds will not fall into the class of agents which exhibit the most preferred binding affinity.

Chelating groups that are analogs of 1,2-diaminocyclohexaneacetic acid are particularly preferred for use in the practice of this invention. The chelating group is covalently bonded, generally though not necessarily through an appropriate bridging entity, to a diagnostic or therapeutic molecule of interest to create agents useful in the practice of the invention. The chelating portion provides a strong bonding site for metal ions and, by selecting the proper linking structure, can be coupled to a variety of sites on a wide range of molecules.

One advantage of 1,2-diaminocyclohexaneacetic acid analogs is that they can be successfully used with polynucleotides and nucleic acids, unlike certain prior art aromatic chelating groups which cannot usually be used with polynucleotides because of intercalation. The cyclohexane-based dicyclohexanetetraacetic acid (DCTA) analogs generally do not interfere with any normal reactions of labeled polynucleotides or nucleic acids and can additionally be used with any of the other molecularly recognizable portions disclosed herein. The DCTA analogs also have binding affinities for metal ions several orders of magnitude higher than those of EDTA.

Examples of therapeutic and diagnostic agents useful in this invention are also disclosed and discussed in U.S. Pat. No. 4,707,440 which is herein incorporated by reference in its entirety.

The chemical structure of the preferred chelating groups in a diagnostic or therapeutic agent as described herein is exemplified by the following structural formula:

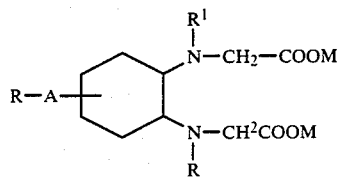

wherein R is the substantially non-metal chelating portion of the therapeutic or diagnostic agent, $R^1$ is $C_1$-$C_4$ alkyl or is $-CH_2COOM$, M is H or a catonic metal or a negative charge, and A is either a direct covalent bond or a bridging entity such as, e.g., of the type shown in the aforementioned co-pending application. Since spacing is the main consideration rather than the structure of the bridging entity, the chemical structure of the bridging entity is unimportant and is not limited as long as—among other things—molecular recognition is not unduly hindered.

It is preferred to use a bridging entity to join the non-chelating molecule to the chelating molecule from which the chelating portion is derived. The selection of the bridging entity is, of course, varied depending on the type of molecules involved, the number and nature of the available bonding sites, the types of reactions which the labeled agent is to undergo, and/other factors known to those skilled in the art. The linking group can be tailored to specific types of agents, for example, nucleotides, proteins, amino acids, enzymes, etc., to suit the needs of particular detection, imaging, or therapeutic techniques.

Examples of generally useful linking groups include beta-thiopropionic acid hydrazide, beta-thioethylamine, and isothiocyanate. In particular, beta-thiopropionic acid hydrazide has been found to be highly suitable for the attachment of chelating groups to amine-containing molecules under mild conditions. The preferred bridging entity for a particular non-chelating molecule depends on the reactive functional groups present in that molecule. For example, molecules having a free amino group (such as proteins and peptides having one or more lysine residues) can be reacted with a carbonyl azide to form a peptide bond. Molecules having a free hydroxyl group (such as proteins having a tyrosine residue) can be reacted with an isothiocyanate or can be heated in the presence of the azide (which rearranges to form an isocyanate) to form a thiourethane or urethane. Molecules having a carbonyl group can form a Schiff base with an amino group of a modified chelating molecule which can then be reduced if desired to a secondary amine. Many variations of these bonding techniques exist and may be used as deemed appropriate.

Examples of agents which can be used in the practice of the invention include those in which a molecularly recognizable portion is derived from a nucleotide or related compound. Methods of forming such compounds are described in detail and claimed in copending application Ser. No. 391,441, filed June 23, 1982, which is herein incorporated by reference. Accordingly, agents whose molecularly recognizable portion is derived from DNA, RNA, a nucleotide, a deoxynucleotide, nucleoside, or a deoxynucleoside can easily be prepared using the methods described therein for modifying the nucleotide or related molecule, together with the methods described herein for coupling to chelating groups.

The ratio of the non-chelating portion of the agent to the chelating portion need not necessarily be 1:1. There may be many more chelating portions than non-chelating portions, or vice versa. In the case when the ratio of chelating portions to nonchelating portions is greater than 1, for example, 5–10 to 1 or even greater, the system amplifies the radiation provided by the primary recognition event by a factor equal to the ratio.

It should again be noted that the aspect of the present invention relating to labeling an agent already containing a chelating portion in no way depends upon the structure of the molecules being manipulated but rather depends on their chelating ability and their ability to be recognized on a molecular scale in a biological or biochemical system. So long as chelation with radioactive metal ion is possible, molecular recognition can take place, and an ion transfer material is available which has a lower binding affinity for the radioactive metal than does the chelating portion of the agent, the invention can be practiced regardless of the structure of the molecule.

Likewise, the structure of the ion-transfer material is unimportant so long as the binding affinity (i.e., the binding function) is within the limitations disclosed. Although, generally speaking, it is sufficient for the practice of this invention to use an ion transfer material whose binding affinity for the radioactive metal ion is merely less than the binding affinity of the therapeutic or diagnostic agent for the same ion, it is preferred that the ratio of binding affinities be less than 0.1, more preferably less than 0.01, and most preferably less than 0.001, in order to ensure effective transfer of the radioactive metal ion from the ion transfer material to the agent.

Suitable ion transfer materials include both inorganic and synthetic organic products. Inorganic ion transfer materials include both the naturally occurring materials (e.g., mineral zeolites such as sodalite and clinoptilolite, the green sands, and clays such as the montmorillonite group), and synthetic products such as the gel zeolites, dehydroxides of polyvalent metals such as hydrated zirconium oxide, and the insoluble salts of polybasic acids with polyvalent metals such as zirconium phosphate. Preferred ion transfer materials are the synthetic organic cation exchange resins. These include weak-acid, cation-exchange resins and strong-acid resins. The weak-acid resins are generally based on acrylic or methacrylic acid that has been crosslinked with a difunctional vinyl monomer, such as divinyl benzene. Other weak-acid groups, such as phenolic or phosphonic functional groups, may also be used. The weak-acid resins are generally used at a pH above 4. The strong-acid resins are generally based on sulfonated copolymers of styrene and divinyl benzene. These materials are particularly preferred because of their ability to exchange cations across the entire pH range. The most preferred ion exchange materials are sufficiently porous to provide a large surface area on which exchange can take place. Pore sizes are preferably sufficient to allow easy passage of the agent through the pores and most preferably are several times the largest diameter of the molecule in question. However, if the diagnostic or therapeutic agent is particularly large, transfer may occur on exterior surfaces only.

Many commercially available ion transfer materials are known and may be used in the practice of this invention if the guidelines set forth herein are followed. For example, Dowex 50 and materials having similar properties are particularly suitable.

In general, the labeling process of the present invention is accomplished by contacting the therapeutic or diagnostic agent as defined herein with an ion transfer material having the radioactive element bound thereto. The contacting may consist either of passing a solution containing the agent over a column of the ion transfer material or by suspending the ion transfer material in a solution of the agent. Although these methods of contacting are preferred, any other method of intimately contacting a solution containing the agent with the ion transfer material is suitable. The amount of radioactivity bound to the ion transfer material, the duration of the contact time, and the ratio of the amount of the diagnostic agent to the amount of the ion transfer material, as well as other conditions, vary depending on the amount of radioactivity needed for the particular situation in which the agent is to be used, as is well understood to those skilled in the art. If the conditions and contacting times are not known, they can easily be determined by simple experimentation. After a sufficient contacting time, the radioactivity labeled agent is separated from the ion transfer material by any suitable technique. Typically, the ion transfer material will be present in the form of a column and the agent can be separated by elution. Elution can occur using the solvent in which contacting took place, or a second eluent may be used if such treatment more easily dislodges the agent from the ion transfer material. If not already known, suitable eluents may be determined by simple experimentation since elution of radioactivity is easily followed. It is particularly preferred that an eluent not permanently change a molecularly recognizable portion of the agent so that the recognition event can no longer take place. However, a temporary change, for example in conformation, causes no harm if the recognizable structure can later be regained. Thus elutions with solvents or solutions, or under conditions which result in a reversible conformational change in the structure of a peptide, for example, are acceptable. Nevertheless, elutions of agents of biological origin at or near physiological conditions (e.g., pH, ionic strength, temperature, etc.) is preferred, particularly if the eluent is to be directly in one of the diagnostic or therapeutic procedures which are later discussed.

Any radioactive metal ion capable of producing a therapeutic or diagnostic result in a human or animal body or in an in vitro diagnostic assay may be used in the practice of the present invention. Suitable ions including the following:

| | | |
|---|---|---|
| Antimony-124 | Iodine-125 | Scandium-44 |
| Antimony-125 | Iodine-131 | Scandium-46 |
| Arsenic-74 | Iridium-192 | Selenium-75 |
| | Iron-55 | Silver-110 m |
| Barium-103 | Iron-59 | Silver-111 |
| Barium-140 | | Sodium-22 |
| Beryllium-7 | Krypton-85 | Strontium-85 |
| Bismuth-206 | | Strontium-89 |
| Bismuth-207 | Lead-210 | Strontium-90 |
| | Lutecium-177 | Sulphur-35 |
| Cadmium-109 | | |
| Cadmium-115 m | Manganese-54 | Tantalum-182 |
| Calcium-45 | Mercury-197 | Technetium-99 |
| | Mercury-203 | Tellurium-125 m |
| Cerium-139 | Molybdenum-99 | Tellurium-132 |
| Cerium-141 | | Terbium-160 |
| Cerium-144 | Neodynium-147 | Thallium-204 |
| Cesium-137 | Neptunium-237 | Thorium-228 |
| Chlorine-36 | Nickel-63 | Thorium-232 |
| Chromium-51 | Niobium-95 | Thulium-170 |
| Cobalt-56 | | Tin-113 |
| Cobalt-57 | Osmium-185 + 191 | Titanium-44 |
| Cobalt-58 | | |
| Cobalt-60 | Palladium-103 | Tungsten-185 |
| Erbium | Platinum-195 m | Vanadium-48 |
| Europium-152 | Praseodymium-143 | Vanadium-49 |
| | Promethium-147 | |
| Gadolinium-153 | Protactinium-233 | Ytterbium-169 |
| Gold-195 | | Yttrium-88 |
| Gold-199 | Radium-226 | Yttrium-90 |
| | Rhenium-186 | Yttrium-91 |
| Hafnium-175 | Rubidium-86 | |
| Hafnium-175 + 181 | Ruthenium-103 | Zinc-65 |
| Hafnium-181 | Ruthenium-106 | Zirconium-95 |

The following non-limiting example illustrates the preparation of a diagnostic or therapeutic agent using a Dowex 50 column. The column is first equilibrated with a dilute solution of a buffer, for example, 0.05 M ammonium acetate and then loaded with a radioactive ion, for example, nickel-63, by passing a solution of the ion through the column. After the column is prepared (when presented in kit form, as later described, the column would be prepared by one other than the ultimate user during preparation of the kit), the agent having a chelating portion is passed through the column and eluted as the radiolabeled metal chelate.

The labeling procedure described above is particularly useful in combination with established therapeutic and diagnostic techniques which use an agent having the properties described in this application. For example, a diagnostic agent useful in radioimmunoassay (RIA) can be labeled immediately prior to its use, thus greatly reducing non-specific binding caused by radiation damage which would occur with an agent which had been labeled and stored for a long period of time. RIA is a well-known technique and will not be described in detail here. For particulars, reference is made to Chard, "An Introduction to Radioimmunoassay and Related Techniques," North-Holland Publishing Company, 1978, which is herein incorporated by reference. Any of the many variations of RIA can be used, such as homogeneous phase RIA, heterogeneous or solid phase RIA, single antibody or double antibody methods, and direct (forward) or reverse sandwich assays. Particularly preferred are solid phase systems wherein the antibody (IgG or IgM) is covalently coupled to an insoluble support so that both the antibody and the bound complex after incubation can be readily separated from the soluble free fraction. A wide variety of solid phase supports have been described, which include particles of dextran or cellulose, continuous surfaces such as polystyrene or polypropylene discs, walls of plastic tubes, glass discs, glass particles, and the like. Particulate solid phases are widely used for a variety of different assays and can be used in the practice of the present invention. Antibodies are attached to the particles by any of a number of techniques designed to yield a non-reversible covalent or non-covalent link between protein and particle, for example, directly or by cyanogen bromide activation. Other alternatives are the use of antibodies entrapped in the interstices of a polyacrylamide gel or bound to magnetic particles. An assay tube is set up containing either sample or standard, along with the tracer and an appropriate amount of solid phase bound antibody, plus a detergent to prevent aggregation of the particles and non-specific absorption of the tracer. After an incubation period during which the tubes are continuously mixed, the solid phase is sedimented by centrifugation; the supernatant is removed and the solid phase subject to two or more washes with buffer in order to remove free tracer trapped within and between the particles. The counts on the solid phase (bound fraction) are then measured. Immunoradiometric assays, as described in Chard at page 423, can also be used. When a second antibody is used, the second antibody can be either IgM or IgG. The present invention is not limited to any of these techniques in particular.

Similarly, the method can be applied in vivo diagnostic and therapeutic techniques by labeling the agent immediately prior to its use. This aspect of the invention is especially important because of the high levels of radioactivity associated with such agents, especially therapeutic agents, which result in rapid degradation of any molecularly recognizable portion of the molecules and loss of specificity. By using the technique of this invention in combination with established in vivo techniques for using radioactive agents, destruction of any molecularly recognizable portion of the agent, which reacts with a complementary substance in a human or animal body to cause selective localization in a target region, is greatly reduced. Accordingly, it is possible in many cases to use a lower total mount of the radioactive isotope in a diagnostic technique because of increased specificity. This technique is particularly suited to use with monoclonal antibodies to which a chelating group is attached.

The present invention lends itself readily to the preparation of kits comprising one or more of the elements necessary to perform the labeling process. Thus, a kit may comprise a carrier being compartmentalized to receive in close confinement therein one or more container means or series of container means such as test tubes, vials, flasks, bottles, syringes, or the like. A first of said container means or series of container means may contain the therapeutic or diagnostic agent as described herein. A second container means or series of container means may contain an ion transfer material capable of binding the radioactive metal ion of interest for the particular application of interest. Two embodiments for the second container means are possible with regard to the radioactive metal itself. In one embodiment, the ion is bound to the ion transfer material during the process of manufacturing the kit. The user of such a kit is therefore not required to handle radioactive material in fluid form at any point prior to obtaining the diagnostic or therapeutic agent in the eluting fluid, which can be chosen so that it is immediately useable. Alternatively, the kit may provide an ion transfer material not having any radioactive metal ion bound thereto. This greatly simplifies preparation, storage, and handling of the kit itself. The radioactive metal ion is then bound to the ion transfer material by the user of the kit. The ion transfer material may then be utilized to label several doses or aliquots of the therapeutic or diagnostic agent. Such a kit and procedure is particularly suited for isotopes of very short lifetimes, such as are often used in in vivo procedures. Medical technicians who would normally use solution chemistry to label a therapeutic agent comprising a chelating portion and an antibody, for example, can accomplish the same result using the techniques of this invention and a kit adapted to that use with less waste radioactivity and contaminated glassware.

It is preferred that the second container means be fitted with fluid inlet and outlet means whereby the agent (unlabeled with radioactivity), when inserted into the inlet means, intimately contacts the ion transfer material while passing through or being contained within said container means prior to exiting through the outlet means. It is particularly preferred that the inlet and outlet means be fitted with confining means, such as a screen, which prevent the exit of the ion transfer material from the container. In a particularly preferred embodiment of the present invention, the second container means containing the ion transfer material having the radioactive ion bound thereto is columnar or tubular in form, with the inlet and outlet means being at opposite ends of the tube. Thus, a user can easily label any diagnostic or therpeutic agent having a chelating portion thereon by adding the agent through the inlet means and removing the agent as it exits the outlet means. Typically, passage of the agent through the container means would occur in solution, whereby the agent would intimately contact ion transfer material therein. The radiolabeled agent can be recovered either by force of pressure or suction or by allowing it to drain from the lower exit means or by passing an eluting fluid through the column, as is well understood by those skilled in the art. One suitable technique would be to use a disposable syringe or other administering means suitable for use in the diagnostic or therapeutic procedure for which a radioactive agent is desired which is fitted with connecting means by which it can be attached to the it means of the ion transfer material container. The agent can then be withdrawn into the syringe with minimum danger of loss or contamination. Typically, the kit would also contain a third container means having therein an eluant suitable for eluting the agent from the column. If the kit is intended for a particular in vitro diagnostic technique, for example, a competitive radioimmunoassay procedure, a fourth container means can contain a complementary substance capable of binding with any molecularly recognizable portion of the agent, for example, a solid phase antibody capable of binding both with the analyte and the diagnostic agent. If the unlabeled resent in a dry form (e.g., lyophilized), a fifth containing means containing a solvent may be supplied. A typical complete kit of the invention will contain at least the first two container means and associated substances and may optionally contain any other related materials useful for the procedure under consideration.

What is claimed as new and desired to be secured by Letters Patent of the United States is:

1. An in vivo diagnostic method, which comprises:
   (1) forming a diagnostic agent labeled with a radioactive metal ion by contacting
      (i) an unlabeled diagnostic agent comprising (a) a molecularly recognizable portion attached to (b) a chelating portion capable of substantially chelating with said radioactive metal ion, wherein said chelating portion is not a part of said molecularly recognizable portion, with (ii) an ion transfer material having said radioactive metal ion bound thereto and having a binding affinity for said radioactive metal ion less than the binding affinity of said chelating portion for said radioactive metal ion.

wherein, prior to said contacting, said chelating portion is unchelated or is chelated with a second metal having a binding affinity with said chelating portion less than the binding affinity of said radioactive metal ion, whereby a radiolabeled diagnostic agent is formed by said contacting; and (2) separtating, if necessary, said ion transfer material from said radiolabeled diagnostic agent;

(3) administering said agent to a human or animal; and (4) detecting radiation emitted by said radioactive metal ion.

2. The method of claim 1, wherein said radiation is gamma radiation.

3. The method of claim 1, wherein said agent selectively localizes in a target region of said human or animal by interaction of a molecularly recognizable portion of said agent with a complementary substance in said target region.

4. The method of claim 3, wherein said complementary substance is a polynucleotide sequence, antigen, antibody, sugar, hormone, hormone receptor, enzyme, enzyme substrate or enzyme cofactor.

5. The method of claim 3, wherein the molecularly recognizable portion of said agent is an antibody.

6. The method of claim 1, wherein the chelating portion of said agent comprises 1,2-diaminocyclohexaneacetic acid or an analogue thereof.

7. A therapeutic process which comprises:

(1) forming a therapeutic agent labeled with a radioactive metal ion by contacting (i) an unlabeled therapeutic agent comprising (a) a molecularly recognizable portion attached to (b) a chelating portion capable of substantially chelating with said radioactive metal ion, wherein said chelating portion is not a part of said molecularly recognizable portion, with (ii) an ion transfer material having said radioactive metal ion bound thereto and having a binding affinity for said radioactive metal ion less than the binding affinity of said chelating portion for said radioactive metal ion.

wherein, prior to said contacting, said chelating portion is unchelated or is chelated with a second metal having a binding affinity with said chelating portion less than the binding affinity of said radioactive metal ion, whereby a radiolabeled therapeutic agent is formed by said contacting; and (2) separating, if necessary, said ion transfer material radiolabeled therapeutic agent;

(3) administering said agent to a human or animal wherein said agent selectively localizes in a target region of said human or animal, therety concentrating radiation from said radioactive metal ion in said target region.

8. The process of claim 7, wherein said radiation is beta radiation.

9. The method of claim 7, wherein said agent localizes in a target region of said human or animal by interaction of a molecularly recognizable portion of said agent with a complementary substance in said target region.

10. The method of claim 9, wherein said complementary substance is a polynucleotide sequence, antigen, antibody, sugar, hormone, hormone receptor, enzyme, enzyme substrate or enzyme cofactor.

11. The method of claim 9, wherein the molecularly recognizable portion of said agent is an antibody.

12. The method of claim 7, wherein the chelating portion of said agent comprises 1,2-diaminocyclohexaneacetic acid or an analogue thereof.

13. A kit suitable for forming an in vivo therapeutic or diagnostic agent labeled with a radioactive metal ion, which comprises:

(A) carrier means compartmentalized to receive in close confinement therein one or more containers;

(B) a first container confined within said carrier and containing a therapeutic or diagnostic agent consisting of (1) a substantially non-metal chelating portion attached to (2) a chelating portion capable of chelating with a radioactive metal ion; and (C) a second container confined within said carrier and containing an ion transfer material capable of binding said radioactive metal ion bound thereto wherein the binding affinity of said ion transfer material for said radioactive metal ion is less than the binding affinity of said chelating portion for said radioactive metal ion.

14. The kit of claim 13, wherein said radioactive metal ion is bound to said ion transfer material in said second container.

15. The kit of claim 13, wherein said second container (C) is fitted with fluid inlet and outlet means and with confining means which prevent the exit of said ion transfer material from said second container (C).

16. The kit of claim 13, wherein said second container (C) is columnar with said inlet and outlet means being at opposite ends and said confining means confine said ion transfer material between said inlet means and said outlet means wherein fluid inserted into said inlet means intimately contacts said ion transfer material while passing through said container means prior to exiting through said outlet means.

17. The kit of claim 13, wherein said ion transfer material is a strong-acid cation-exchange resin.

18. The kit of claim 17, wherein said resin is a sulfonated copolymer of styrene and a diene crosslinking agent.

19. The kit of claim 18, wherein said crosslinking agent is divinylbenzene.

20. The kit of claim 19, wherein said resin is porous.

21. The kit of claim 13, wherein the substantially non-metal chelating portion of said agent comprises an antibody, hormone, enzyme, enzyme substrate, enzyme cofactor, lipid, saccharide, polynucleotide sequence, virus, virus fragment, cell, or cell fragment.

22. The kit of claim 21, wherein said substantially non-metal chelating portion comprises an antibody.

23. The kit of claim 21, wherein said substantailly non-metal chelating portion comprises a polynucleotide sequence.

24. The kit of claim 13, wherein the chelating portion of said agent comprises 1,2-diaminocyclohexaneacetic acid or an analogue thereof.

25. The kit of claim 13, wherein said kit further comprises a third container confined within said carrier means and containing an eluent capable of eluting said agent from said ion transfer material.

26. The kit of claim 13, wherein said kit further comprises administering means, whereby said agent can be administered to a human or animal by use of said administering means.

27. The kit of claim 26, wherein said administering means is a disposable syringe adapted for accepting said agent as said agent exits from said second container (C).

* * * * *